United States Patent
Appel et al.

(10) Patent No.: US 10,112,889 B2
(45) Date of Patent: Oct. 30, 2018

(54) CONTINUOUS PROCESS FOR PRODUCING A SURFACTANT IN A TUBE REACTOR

(71) Applicant: Clariant International Ltd., Muttenz (CH)

(72) Inventors: Jörg Appel, Tüßling (DE); Dennis Heitmann, Grabenstätt (DE); Sarah Werner, Mühldorf (DE)

(73) Assignee: CLARIANT INTERNATIONAL LTD., Muttenz (CH)

( * ) Notice: Subject to any disclaimer, the term of this patent is extended or adjusted under 35 U.S.C. 154(b) by 0 days.

(21) Appl. No.: 15/526,464

(22) PCT Filed: Nov. 9, 2015

(86) PCT No.: PCT/EP2015/076072
§ 371 (c)(1),
(2) Date: May 12, 2017

(87) PCT Pub. No.: WO2016/075080
PCT Pub. Date: May 19, 2016

(65) Prior Publication Data
US 2017/0305838 A1    Oct. 26, 2017

(30) Foreign Application Priority Data

Nov. 13, 2014 (DE) .......... 10 2014 016 841
May 11, 2015 (DE) .......... 10 2015 006 119

(51) Int. Cl.
| C07C 231/02 | (2006.01) |
| B01J 19/18 | (2006.01) |
| B01J 19/24 | (2006.01) |
| C07C 231/00 | (2006.01) |

(52) U.S. Cl.
CPC ......... C07C 231/02 (2013.01); B01J 19/1812 (2013.01); B01J 19/242 (2013.01); C07C 231/00 (2013.01); *B01J 2219/24* (2013.01)

(58) Field of Classification Search
CPC ... C07C 231/02; C07C 231/00; B01J 19/1812
See application file for complete search history.

(56) References Cited

U.S. PATENT DOCUMENTS

| 4,681,946 A | * | 7/1987 | Baur | C07D 213/81 546/317 |
| 5,194,639 A | * | 3/1993 | Connor | C07C 231/02 554/66 |
| 5,539,134 A | * | 7/1996 | Strecker | C07C 231/02 554/66 |
| 5,625,098 A | * | 4/1997 | Kao | C07C 213/02 564/480 |
| 5,777,165 A | * | 7/1998 | Kao | C07C 231/02 544/187 |
| 2001/0023298 A1 | * | 9/2001 | Weinelt | C07C 231/02 554/61 |

FOREIGN PATENT DOCUMENTS

| CA | 2127644 | * | 1/1995 | .......... C07C 233/17 |
| EP | 0633244 | | 1/1995 | |

OTHER PUBLICATIONS

International Search Report for PCT/EP2015/076072, dated Feb. 29, 2016.
International Preliminary Report on Patentability for PCT/EP2015/076072, dated May 16, 2017.

\* cited by examiner

*Primary Examiner* — Yate' K Cutliff
(74) *Attorney, Agent, or Firm* — Tod A. Waldrop

(57) ABSTRACT

The invention relates to a continuous method for producing a tenside, containing a compound of the formula (1), wherein $R^2$ is a fatty acid alkyl residue and $R^1$ is a linear or branched $C_1$ to $C_{12}$ hydrocarbon residue, and x is in the range from 1 to 15 by conversion of fatty acid alkyl esters or fatty acid triglycerides having an N-n-alkylized polyhydroxy compound in the presence of an alkali catalyst or a catalyst selected from hydroxides or alcoholates of the 2nd and 4th secondary group of the periodic system at a temperature in the range from 40 to 300° C.

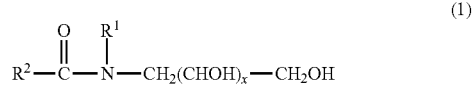

(1)

14 Claims, No Drawings

CONTINUOUS PROCESS FOR PRODUCING A SURFACTANT IN A TUBE REACTOR

The following invention pertains to a continuous operation for preparation of surfactants, more particularly of polyhydroxy-fatty acid amides (e.g. N-methylglucamides), in a tube reactor. Surfactants may be used, for example, as surface-active substances, in laundry detergent formulations, for example. The process of the invention allows surfactants to be prepared continuously with high yield and purity.

BACKGROUND TO THE INVENTION

For use in laundry detergent formulations, personal care products, and in crop protection, there is a great multiplicity of nonionic surfactants. One alternative to many conventional surfactants are polyhydroxy-fatty acid amides, which are valuable surface-active compounds with diverse possible uses.

They can, for example, be used—as they are or in a mixture with anionic, cationic and/or nonionic surfactants—as cleaning agents, laundry detergents, textile treatment agents or the like, and can be used in the form of solid products (for example, as powders, granules, pellets or flakes), solutions, dispersions, emulsions, pastes, and the like. Since polyhydroxy-fatty acid amides are also highly biodegradable and can be prepared from renewable raw materials, they have acquired greater significance in more recent times.

The obvious supposition would therefore be that these compounds have found application in a multiplicity of formulations. However, it is not possible to confirm this supposition. As a reason for this fact, it is assumed that the preparation of these polyhydroxy-fatty acid amides, particularly in the desired quality and purity, is too demanding. The batch-process preparation of polyhydroxy-fatty acid amides has indeed been copiously described, but these processes result in unsatisfactory quality. For use in the personal care segment in particular, a strict specification must be complied with in relation, for example, to color, solvent content, and secondary components. This is not possible by an economic route with the processes described in the literature. In particular, high residence times with severe temperature exposure, poor mixing, and severe foaming in a batchwise-operated process may give rise to considerable problems.

Preparation in a batch process allows the various requirements to be addressed specifically during the reaction. Thus there may be different rheological phases, lasting for different lengths of time according to product. A continuous process has to master this challenge, and this is one reason why to date there have been no continuous processes described that achieve the stated quality requirements.

EP 0633244 A2 describes the operation of a stirred tank cascade for the preparation of polyhydroxy-fatty acid amides. That operation, however, has the disadvantage of a broad residence time distribution, leading to increased formation of undesirable byproducts. In view of the high reaction volumes and associated adverse temperature distribution in the reaction system, the thermal exposure is too high, with adverse consequences for the color of the products.

This operation, moreover, has the disadvantage of severe foaming during the removal of the coproducts. As a result of the foaming, the desired low pressure for complete removal of the coproducts cannot be attained. In order to ensure removal of the coproducts, it would be necessary to use a higher temperature and/or a lower throughput, resulting in a higher temperature exposure of the end product. High temperature exposure, however, leads to a greater amount of secondary components and to a poorer color.

In order to overcome the problems identified above, a new, continuous process has been developed in which polyhydroxy-fatty acid amides can be prepared with improved quality and in greater yields by virtue of a shortened residence time and optimized temperature control. The improved quality is evident not least in a reduction of coloring substances and of secondary components (GCN<3, cyclic material <0.1%). With the new process, furthermore, it is possible to ensure an MeOH content of <0.3% in the end product.

DESCRIPTION OF THE INVENTION

Surprisingly it has now been found that the preparation of surfactants, especially of polyhydroxy-fatty acid amides, is possible more economically and with higher product quality with the continuous process of the invention.

Because the product is highly temperature-sensitive, especially with regard to the amount of cyclic amides and the color of the product, a continuous preparation operation in a tube reactor with low residence time is a significantly better alternative in order to achieve very good product quality. By this means, moreover, the preparation costs can be lowered.

The present invention is directed to a continuous operation for preparing a surfactant which possesses a high fraction of the compound of the formula (1) in which $R^2$ is a fatty acid alkyl radical and $R^1$ is a straight-chain (linear) or branched $C_1$ to $C_{12}$, preferably a $C_1$ to $C_8$, more particularly a $C_1$-$C_6$ hydrocarbyl radical, as for example a methyl, ethyl, propanyl, isopropyl, n-butanyl or isobutyl radical. Preferred in particular are methyl and ethyl; especially methyl. X is in the range from 1 to 15, more particularly 2 to 6.

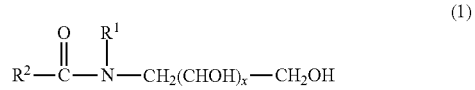
(1)

by reacting fatty acid alkyl esters or fatty acid triglycerides with an N-n-alkylated polyhydroxy compound in the presence of an alkali metal catalyst or of a catalyst selected from hydroxides or alkoxides of transition groups 2 and 4 of the Periodic Table at a temperature in the range from 40 to 300° C.

The fraction of the compound (1) in the surfactant is customarily in the range from 15 to 100 wt %, preferably in the range from 30 to 100 wt %.

The operation comprises reaction of fatty acid alkyl esters or fatty acid triglycerides of chain lengths $C_4$ to $C_{50}$, preferably $C_6$ to $C_{28}$, more particularly $C_6$ to $C_{20}$, and N-alkylglucamines in the presence of alkali metal catalysts, preferably alkali metal hydroxides and alkali metal alkoxides, more particularly sodium hydroxide, sodium methoxide, sodium ethoxide, potassium hydroxide or potassium methoxide, potassium ethoxide as catalyst in a continuous tube reactor. Other catalysts which can be used are hydroxides or alkoxides of transition groups 2 and 4 of the Periodic Table, such as titanium tetraisopropoxide, for example.

The operation according to the invention converts N-alkylglucamines, e.g., N-methyl D-glucamines, into linear glucamide surfactants of very high quality, which even without a further processing step (e.g., recrystallization) are suitable for use in the personal care sector.

The process of the invention comprises 4 to 7 operating steps, 1. mixing the aqueous N-alkylglucamine raw material solution (concentration 30-90 wt %, amine in water) with 0.01-5 wt %, preferably 0.05-4 wt %, more particularly 1-3 wt % of catalyst, with mixing being possible in any order.

The temperature during mixing ought to be 40-120° C., preferably 50-100° C., more particularly 50-90° C., with mixing taking place at a pressure of 0-6 bar, but normally under atmospheric pressure.

2. drying the aqueous solution. The drying ought to be as effective as possible and ought not to exceed a water content after drying of 0-5 wt %, preferably 0-3 wt %, and more particularly 0-1 wt %.

The temperature during drying (2) is 80-180° C.; preferably 90-160° C.; more particularly 100-150° C., it being possible to operate either under atmospheric pressure or else under reduced pressure. The pressure during this step is customarily in the range of 0-2 bar, preferably 0-1 bar; more particularly 0.01-1 bar.

3. heating the dried N-alkylglucamine mixture to a temperature in the range of 60-180° C., preferably 70-160° C.; more particularly 80-150° C., at a pressure in the range of 0-6 bar, and mixing the N-alkylglucamine melt with fatty acid alkyl esters in a molar N-alkylglucamine melt:fatty acid alkyl ester ratio of 1:0.85 to 1:1.2, preferably 1:0.9 to 1.15, more preferably 1:0.95 to 1:1.1, or, when using triglycerides, in a molar N-alkylglycamine melt:triglycerol ratio of 0.25:1 to 0.45:1, preferably of 0.3:1 to 0.4:1, more particularly of 0.33:1 to 0.37:1. The average residence time here is customarily in the range from 1 minute to 2 hours; preferably 2 min to 1 h; more particularly 5-45 minutes.

4. (optionally) intermediately storing and mixing the reaction mixture in a continuously operated stirred tank. In this case the temperature in the stirred tank is customarily 60-300° C.; preferably 70-200° C.; more particularly 80-150° C., at pressures of 0-200 bar, preferably 0.5-80 bar, more particularly at 1-5 bar.

5. The reaction in the tube reactor takes place at a temperature in the range of 60-300° C.; preferably 70-200° C.; more particularly at 80-150° C., at pressures of 0-200 bar, preferably 0.5-80 bar, more particularly at 1-20 bar. The average residence time in this case is customarily in the range from 2 minutes to 2 hours; preferably 2 minutes to 1 hour; more particularly 5-45 minutes, and optionally 6. removing the coproducts. The removal of the coproducts is optional and takes place at a temperature in the range of 50-180° C.; preferably at 60-160° C.; more particularly at 70-150° C. The applied pressure here may range from atmospheric pressure to reduced pressure and is customarily 0-2 bar, preferably 0-1 bar; more particularly 0.01-1 bar. Customarily the coproducts are removed by methods known to the skilled person, such as by continuous distillation or by means of a thin-film evaporator (also flash evaporator or falling-film evaporator).

7. (optionally) formulating the product:

For greater ease of handling in subsequent processing steps, the products obtained as per operation according to the invention, of the formula (1), can be blended (formulated) with various solvents such as water, alcohols (e.g., ethanol, isopropanol, cetearyl alcohol), glycols (ethylene glycol, propylene glycol, polypropylene glycols, polyethylene glycols) and mixtures thereof, and also with additives such as preservatives (e.g., methylisothiazolinone; benzoic acid, sorbic acid) and substances for adjusting the pH (e.g., citric acid, lactic acid, benzoic acid, et cetera). This is done customarily at temperatures in the range from 10 to 130° C.; preferably at 20 to 110° C. under atmospheric pressure.

It has emerged that in the respective reactors, there is a temperature difference between the reactor wall and the core flow of <20° C. This temperature difference ought preferably to be <10° C., more particularly <5° C., in order to ensure the desired high quality and purity of the products.

The alcohol that is formed during the reaction can be separated off via a continuously operated thin-film evaporator or similar apparatus known to the skilled person. One of the advantages of the process of the invention is that throughout the operation there is little or no foaming. In the case of reactions in which N-alkylglucamine is reacted with triglycerides, the last reaction step is not necessary. In this case, glycerol is formed as a coproduct, and can remain in the end product. If the N-alkylglucamines are in the form of an aqueous solution, a melt is prepared by means of a continuous drying process (e.g., thin-film evaporator).

In the mixer, depending on the mode of its construction, it is necessary to enable a high phase interface and/or to ensure effective phase exchange by adding small amounts (0-10%) of phase transfer substances. In accordance with the invention, the phase transfer substances may be added in the first three steps, i.e., 1, 2 or 3. Examples of possible phase transfer substances include water and/or alcohols (ethanol, methanol, propanol, isopropanol, butanol, isobutanol), glycols (propylene glycol, monoethylene glycol), n-alkylglucamides, polyalkyl glycols, crown ethers, glycerol. The concentration of the phase transfer substances in the end product is customarily between 0-30%, preferably 0-20%, and more particularly 0-10%.

The continuous process of the invention has a number of advantages over the processes described in the prior art:

Plant capacity is increased, owing to the omission of the sequential operation of the individual handling steps (charging, reaction, methanol removal, discharging, heating, cooling).

The operation according to the invention can therefore be automated more easily and can be operated with reduced staffing. Moreover, the space-time yield is increased and the reaction times become shorter, leading to a narrower residence time distribution in contrast to batchwise operation. Moreover, product quality can be reproduced more effectively and is less variable, as evidenced in particular in the high purity of the products obtained. Thus the compounds of the formula (1) that are obtained in accordance with the invention have Gardner color numbers of 0 to 3, preferably of 0.1 to 2.5, more particularly of 0.3 to 2.0, which are thus improved significantly relative to the products obtained in the batch process, as is also demonstrated by the examples which follow. The fraction of cyclic secondary components as well, with a fraction of <0.05 wt %, preferably <0.03 wt %, more particularly <0.02 wt %, is also much lower than in the case of the known processes. As a result, the products obtained can be used without further purification even in applications where requirements are exacting (e.g. personal care).

EXAMPLES

Example 1: Cocoylglucamide from Aqueous N-Methylglucamine Solution and Coconut Oil N-Methylglucamine melt at a temperature of 135° C. is prepared from aqueous N-methylglucamine solution with sodium hydroxide via a thin-film evaporator operated continuously at 145° C. This melt is mixed with a coconut oil melt (Gustavheess (material number: 204403)) at a temperature of 40° C. using a static mixer at 130° C. The mixture is stored temporarily in a continuous stirred reactor and subsequently reacted in a tube reactor. The residence times are 35 minutes in the stirred reactor and 11 minutes in the tube reactor. The temperature in the stirred vessel is 130° C.; the temperature in the tube reactor is 100° C. At the end of the tube reactor, the finished product can be discharged without further workup.

Example 2: Cocoylglucamide from Aqueous N-Methylglucamine Solution and Coconut Oil using a Phase Transfer Substance An N-methylglucamine melt at a temperature of 135° C. is prepared from aqueous N-methylglucamine solution with sodium hydroxide via a thin-film evaporator operated continuously at 145° C. This melt is mixed with propylene glycol and a coconut oil melt (Gustavheess (material number: 204403)) at a temperature of 40° C. using a static mixer at 130° C. The mixture is stored temporarily in a continuous stirred reactor and subsequently reacted in a tube reactor. The residence times are 25 minutes in the stirred reactor and 8 minutes in the tube reactor. The temperature in the stirred vessel is 100° C.; the temperature in the tube reactor is 95° C. At the end of the tube reactor, the finished product can be discharged without further workup.

Example 3: Oleylglucamide from Aqueous N-Methylglucamine Solution and Sunflower Oil Dried N-methylglucamine melt is prepared from aqueous N-methylglucamine solution with sodium hydroxide via a two-stage stirred tank cascade operated continuously at 135° C. This melt, with addition of propylene glycol and sunflower oil (Cargill (Agripur AP88, material number: 233301)) at a temperature of 80° C., is mixed using a static mixer at 120° C. The mixture is stored temporarily in a continuous stirred reactor and subsequently reacted in a tube reactor. The residence times are 55 minutes in the stirred reactor and 21 minutes in the tube reactor. The temperature in the stirred vessel is 110° C.; the temperature in the tube reactor is 100° C. At the end of the tube reactor, the finished product can be discharged without further workup.

Example 4: Octanoyl/Decanoylglucamide from Aqueous N-Methyl-Glucamine Solution and Octanoyl/Decanoyl Methyl Ester using a Phase Transfer Substance An N-methylglucamine melt at a temperature of 135° C. is prepared from aqueous N-methylglucamine solution with sodium hydroxide via a thin-film evaporator operated continuously at 145° C. This N-methylglucamine melt at a temperature of 135° C., with addition of propylene glycol and octanoyl/decanoyl methyl ester, is mixed via a static mixer at 120° C. The mixture is stored temporarily in a continuous stirred reactor and subsequently reacted in a tube reactor. The residence times are 10 minutes in the stirred reactor and 3 minutes in the tube reactor. The temperature in the stirred vessel is 85° C.; the temperature in the tube reactor is 75° C. In the course of the reaction, methanol is formed, and is separated off via a continuously operated thin-film evaporator, mounted at the tube reactor exit, at 120° C.

Example 5: Octanoyl/Decanoylglucamide from Aqueous N-Methyl-Glucamine Solution and Octanoyl/Decanoyl Methyl Ester An N-methylglucamine melt at a temperature of 135° C. is prepared from aqueous N-methylglucamine solution with sodium hydroxide via a thin-film evaporator operated continuously at 145° C. This N-methylglucamine melt at a temperature of 135° C. is mixed with octanoyl/decanoyl methyl ester via a static mixer at 120° C. The mixture is stored temporarily in a continuous stirred reactor and subsequently reacted in a tube reactor. The residence times are 17 minutes in the stirred reactor and 4 minutes in the tube reactor. The temperature in the stirred vessel is 95° C.; the temperature in the tube reactor is 85° C. In the course of the reaction, methanol is formed, and is separated off via a continuously operated flash evaporator, mounted at the tube reactor exit, at 135° C.

Example 6: n-Lauroyl/n-Myristoyl-N-Methyl-N-Glucamide from Aqueous N-Methylglucamine Solution and Lauric/Myristic Acid Methyl Ester using a Phase Transfer Substance An N-methylglucamine melt at a temperature of 135° C. is prepared from aqueous N-methylglucamine solution with sodium hydroxide via a thin-film evaporator operated continuously at 145° C. This N-methylglucamine melt at a temperature of 135° C., with addition of ethanol as phase transfer substance and lauric/myristic acid methyl ester, is mixed via a static mixer at 120° C. The mixture is reacted in a tube reactor. The residence time is 45 minutes in the tube reactor. The temperature in the tube reactor is 155° C. In the course of the reaction, methanol is formed, and is separated off via a continuously operated column, mounted at the tube reactor exit, at 135° C.

Example 7: n-Lauroyl/n-Myristoyl-N-Methyl-N-Glucamide from Aqueous N-Methylglucamine Solution and Lauric/Myristic Acid Methyl Esters An N-methylglucamine melt at a temperature of 130° C. is prepared from aqueous N-methylglucamine solution with sodium hydroxide via a flash evaporator operated continuously at 140° C. This N-methylglucamine melt at a temperature of 130° C. is mixed with lauric/myristic acid methyl ester via a static mixer at 130° C. The mixture is stored temporarily in a continuous stirred reactor and thereafter reacted in a tube reactor. The residence times are 33 minutes in the stirred reactor and 13 minutes in the tube reactor. The temperature in the stirred vessel is 100° C.; the temperature in the tube reactor is 95° C. Methanol is formed in the reaction, and is separated off via a continuously operated flash evaporator, which is mounted at the tube reactor exit, at 145° C.

Example 8: Hexadecanoyl/Octadecanoyl-N-Methyl-N-Glucamide from Aqueous N-Methylglucamine Solution and Hexadecanoyl/Octadecanoyl Methyl Ester using a Phase Transfer Substance An N-methylglucamine melt at a temperature of 135° C. is prepared from aqueous N-methylglucamine solution with potassium hydroxide via a thin-film evaporator operated continuously at 145° C. This N-methylglucamine melt at a temperature of 135° C. is mixed, with addition of hexadecanoyl/octadecanoyl-N-methyl-N-glucamide as phase transfer substance and hexadecanoyl/octadecanoyl methyl ester via a static mixer at 120° C. The mixture is reacted in a tube reactor. The residence time is 28 minutes in the tube reactor. The temperature in the tube reactor is 105° C. Methanol is formed in the reaction, and is separated off via a continuously operated thin-film evaporator, which is mounted at the tube reactor exit, at 135° C.

Example 9:
Hexadecanoyl/Octadecanoyl-N-Methyl-N-Glucamide from Aqueous N-Methylglucamine Solution and Hexadecanoyl/Octadecanoyl Methyl Ester An N-methylglucamine melt at a temperature of 140° C. is prepared from aqueous N-methylglucamine solution with sodium hydroxide via a thin-film evaporator operated continuously at 145° C. This N-methylglucamine melt at a temperature of 140° C., with addition of propylene glycol as phase transfer substance and hexadecanoyl/octadecanoyl methyl ester, is mixed via a static mixer at 130° C. The mixture is stored temporarily in a continuous stirred reactor and thereafter reacted in a tube reactor. The residence times are 17 minutes is the stirred reactor and 5 minutes in the tube reactor. The temperature in the stirred vessel is 95° C.; the temperature in the tube reactor is 85° C. Methanol is formed in the reaction, and is separated off via a continuously operated thin-film evaporator, which is mounted at the tube reactor exit, at 135° C.

Example 10:
n-Dodecanoyl/n-Docosanoyl-N-Methyl-N-Glucamide from Aqueous N-Methylglucamine Solution and n-Dodecanoyl/n-Docosanoyl Methyl Ester An N-methylglucamine melt at a temperature of 135° C. is prepared from aqueous N-methylglucamine solution with sodium hydroxide via a thin-film evaporator operated continuously at 145° C. This N-methylglucamine melt at a temperature of 135° C., with addition of propylene glycol and n-dodecanoyl/n-docosanoyl methyl ester, is mixed via a static mixer at 120° C. The mixture is stored temporarily in a continuous stirred reactor and thereafter reacted in a tube reactor. The residence times are 20 minutes in the stirred reactor and 9 minutes in the tube reactor. The temperature in the stirred vessel is 88° C.; the temperature in the tube reactor is 78° C. Methanol is formed in the reaction, and is separated off via a continuously operated thin-film evaporator, which is mounted at the tube reactor exit, at 135° C.

Example 11: n-Dodecanoyl-N-Ethyl-N-Glucamide Glucamide from Aqueous N-Ethylglucamine Solution and n-Dodecanoyl Methyl Ester An N-ethylglucamine melt at a temperature of 145° C. is prepared from aqueous N-ethylglucamine solution with sodium hydroxide via a thin-film evaporator operated continuously at 155° C. This N-ethylglucamine melt at a temperature of 145° C., with addition of propylene glycol and n-dodecanoyl methyl ester, is mixed via a static mixer at 120° C. The mixture is stored temporarily in a continuous stirred reactor and thereafter reacted in a tube reactor. The residence times are 44 minutes in the stirred reactor and 28 minutes in the tube reactor. The temperature in the stirred vessel is 105° C.; the temperature in the tube reactor is 95° C. Methanol is formed in the reaction and is separated off via a continuously operated thin-film evaporator, which is mounted at the tube reactor exit, at 135° C.

Example 12: n-Dodecanoyl-N-Octyl-N-Glucamide from Aqueous N-Octyl-Glucamine Solution and n-Dodecanoyl Methyl Ester An N-octylglucamine melt at a temperature of 145° C. is prepared from aqueous N-octylglucamine solution with sodium hydroxide via a thin-film evaporator operated continuously at 155° C. This N-octylglucamine melt at a temperature of 145° C., with addition of propylene glycol and n-dodecanoyl methyl ester, is mixed via a static mixer at 120° C. The mixture is stored temporarily in a continuous stirred reactor and thereafter reacted in a tube reactor. The residence times are 44 minutes in the stirred reactor and 28 minutes in the tube reactor. The temperature in the stirred vessel is 105° C.; the temperature in the tube reactor is 95° C. Methanol is formed in the reaction and is separated off via a continuously operated thin-film evaporator, which is mounted at the tube reactor exit, at 135° C.

Example 13: Batch Mixture:
Octanoyl/Decanoylglucamide from Aqueous N-Methylglucamine Solution and Octanoyl/Decanoyl Methyl Ester An aqueous N-methylglucamine solution with sodium hydroxide is dewatered down to a water content below 1% at 130-135° C. under a pressure of 25-30 mbar. The N-methylglucamine melt is admixed with propylene glycol. Then n-octanoyl/decanoyl methyl ester is metered in at 120° C. The mixture is reacted under reflux conditions in a batchwise-operated stirred reactor. Thereafter the resultant methanol is distilled off under a pressure of between 25 mbar and 1 bar and the subsequent reaction is carried out at 75-85° C. The residence time of the whole reaction is between 3 and 8 h depending on batch size.

Regarding examples 1 to 13:

Examples 1 to 5, 10, and 13 are subsequently formulated with water, citric acid, and a preservative. Examples 6 to 7 are subsequently formulated with water, citric acid, and ethanol. Examples 8 and 9 are formulated with cetearyl alcohol.

In comparison to an experiment in batchwise operation, a significantly improved color was observed on the part of the product. In the batchwise-operated experiment, the Gardner color number (according to EN 1557) was above 3.5. The product from continuous operation has a Gardner color number below 3.5. In the case of the secondary component (cyclic glucamide), a fraction of less than 0.1 wt % was observed. In batch operation, the figure is more than 0.1 wt %. The APHA color numbers were measured according to EN 1557.

Tables for the operating conditions of examples 1 to 12:
Temperatures in ° C.:

| Example | Raw materials mixing | Aqueous solution drying | Melt mixing | Stirred removal | Tube reactor | Co-product reactor |
|---|---|---|---|---|---|---|
| 1 | 70 | 145 | 130 | 130 | 100 | — |
| 2 | 70 | 145 | 130 | 100 | 95 | — |
| 3 | 40 | 135 | 120 | 110 | 100 | — |
| 4 | 40 | 145 | 120 | 85 | 75 | 120 |
| 5 | 80 | 145 | 120 | 95 | 85 | 135 |

-continued

| Example | Raw materials mixing | Aqueous solution drying | Melt mixing | Stirred removal | Tube reactor | Co-product reactor |
|---|---|---|---|---|---|---|
| 6 | 80 | 145 | 120 | — | 155 | 135 |
| 7 | 70 | 140 | 130 | 100 | 95 | 145 |
| 8 | 70 | 145 | 120 | — | 105 | 135 |
| 9 | 70 | 145 | 130 | 95 | 85 | 135 |
| 10 | 70 | 135 | 120 | 88 | 78 | 135 |
| 11 | 70 | 155 | 120 | 105 | 95 | 135 |
| 12 | 70 | 155 | 120 | 105 | 95 | 135 |

Pressures in bar (abs):

| Example | Raw materials mixing | Aqueous solution drying | Melt mixing | Stirred reactor | Tube reactor | Co-product removal |
|---|---|---|---|---|---|---|
| 1 | 1 | 0.1 | 5 | 1 | 15 | — |
| 2 | 1 | 0.1 | 5 | 1 | 13 | — |
| 3 | 2 | 0.1 | 3 | 1 | 15 | — |
| 4 | 1 | 0.1 | 3 | 1 | 7 | 0.01 |
| 5 | 1 | 0.1 | 3 | 1 | 10 | 0.05 |
| 6 | 1 | 0.1 | 3 | — | 53 | 0.05 |
| 7 | 1 | 0.1 | 5 | 1 | 13 | 0.1 |
| 8 | 1 | 0.1 | 3 | — | 17 | 0.05 |
| 9 | 1 | 0.1 | 5 | 1 | 10 | 0.05 |
| 10 | 1 | 0.1 | 3 | 1 | 8 | 0.03 |
| 11 | 1 | 0.2 | 6 | 1 | 13 | 0.03 |
| 12 | 1 | 0.2 | 6 | 1 | 14 | 0.03 |

Volume flows in kg/h:

| Example | NMG/NEG/NOG* (anhydrous) | NaOH/KOH | Phase transfer substance | Ester/triglyceride | Water | Citric acid | Ethanol/cetearyl alcohol |
|---|---|---|---|---|---|---|---|
| 1 | 2 | 0.03 | 0 | 2.4 | 5.1 | 0.04 | 0 |
| 2 | 2 | 0.03 | 0.5 | 2.4 | 5.1 | 0.04 | 0 |
| 3 | 2.9 | 0.05 | 1.9 | 4.5 | 0 | 0 | 0 |
| 4 | 2.9 | 0.04 | 0.6 | 2.7 | 4.4 | 0.06 | 0 |
| 5 | 2.9 | 0.04 | 0 | 2.7 | 4.4 | 0.06 | 0 |
| 6 | 3 | 0.05 | 0.7 | 3.6 | 2.2 | 0.12 | 1 |
| 7 | 3 | 0.05 | 0 | 3.6 | 2.2 | 0.12 | 1 |
| 8 | 2 | 0.06 | 1.5 | 2.6 | 0 | 0 | 5 |
| 9 | 2 | 0.03 | 1 | 2.6 | 0 | 0 | 5 |
| 10 | 1.7 | 0.03 | 0.48 | 2.1 | 6 | 0.02 | 0 |
| 11 | 2 | 0.03 | 0.5 | 2.5 | 0 | 0 | 0 |
| 12 | 2.5 | 0.05 | 0.5 | 2.5 | 0 | 0 | 0 |

*NMG = N-methylglucamine NEG = N-ethylglucamine NOG = N-octyl-glucamine

Volume flows in wt %:

| Example | NMG/NEG/NOG* (anhydrous) | NaOH/KOH | Phase transfer substance | Ester/triglyceride | Water | Citric acid | Ethanol/cetearyl alcohol |
|---|---|---|---|---|---|---|---|
| 1 | 20.9 | 0.3 | 0 | 25.1 | 53.3 | 0.4 | 0 |
| 2 | 19.9 | 0.3 | 5.0 | 23.8 | 50.6 | 0.4 | 0 |
| 3 | 31.0 | 0.5 | 20.3 | 48.1 | 0.0 | 0 | 0 |
| 4 | 27.1 | 0.4 | 5.6 | 25.2 | 41.1 | 0.6 | 0 |
| 5 | 28.7 | 0.4 | 0 | 26.7 | 43.6 | 0.6 | 0 |
| 6 | 28.1 | 0.5 | 6.6 | 33.7 | 20.6 | 1.1 | 9.4 |
| 7 | 30.1 | 0.5 | 0 | 36.1 | 22.1 | 1.2 | 10.0 |
| 8 | 17.9 | 0.5 | 13.4 | 23.3 | 0 | 0 | 44.8 |
| 9 | 18.8 | 0.3 | 9.4 | 24.5 | 0 | 0 | 47.0 |
| 10 | 16.5 | 0.3 | 4.6 | 20.3 | 58.1 | 0.2 | 0 |
| 11 | 39.8 | 0.6 | 9.9 | 49.7 | 0 | 0 | 0 |
| 12 | 45.0 | 0.9 | 9.0 | 45.0 | 0 | 0 | 0 |

*NMG = N-methylglucamine NEG = N-ethylglucamine NOG = N-octyl-glucamine

Mass fractions for batch experiment (in wt %):

| Example | NMG (60% in water) | NaOH/KOH | Phase transfer substance | Ester | Water | Citric acid |
|---|---|---|---|---|---|---|
| 13 | 19.8 | 0.9 | 5.7 | 27.3 | 45.7 | 0.6 |

Results:

| Example | Conversion (%) based on NMG/NEG/NOG | Gardner color number | APHA color number | Methanol (wt %) | Cyclic components (wt %) |
|---|---|---|---|---|---|
| 1 | 96 | 0.6 | 125 | 0 | <0.01 |
| 2 | 98 | 0.6 | 125 | 0 | <0.01 |
| 3 | 98 | 0.4 | 83 | 0 | <0.01 |
| 4 | 94 | 1.7 | 354 | 0.3 | <0.01 |
| 5 | 92 | 0.7 | 146 | 0.1 | <0.01 |
| 6 | 96 | 1.2 | 250 | 0.1 | <0.01 |
| 7 | 95 | 0.3 | 63 | <0.1 | <0.01 |
| 8 | 93 | 0.6 | 125 | 0.2 | <0.01 |
| 9 | 95 | 0.7 | 146 | 0.2 | <0.01 |
| 10 | 97 | 0.4 | 83 | 0.1 | <0.01 |
| 11 | 88 | 1.8 | 375 | 0.2 | <0.02 |
| 12 | 84 | 1.9 | 380 | 0.2 | <0.02 |
| 13 | 90 | 3.6 | 500 | 0.4 | 0.1 |

*NMG = N-methylglucamine NEG = N-ethylglucamine NOG = N-octyl-glucamine

The invention claimed is:

1. A continuous process for preparing a surfactant, wherein the surfactant comprises a compound of the formula (1), in which $R^2$ is a fatty acid alkyl radical and $R^1$ is a straight-chain or branched $C_1$ to $C_{12}$ hydrocarbyl radical and x is in the range from 1 to 15

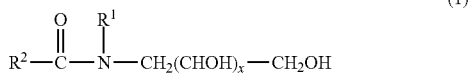
(1)

wherein the continuous process comprises at least the step of reacting at least one fatty acid alkyl ester or fatty acid triglyceride with at least one N-n-alkylated polyhydroxyamine in the presence of an alkali metal catalyst or of a catalyst selected from the group consisting of hydroxides or alkoxides of transition groups 2 and 4 of the Periodic Table, at a temperature in the range from 40 to 300° C., wherein the continuous process comprises the following steps:
1. mixing an aqueous raw material solution comprising at least one N-n-alkylated polyhydroxyamine with the catalyst to form an aqueous solution;
2. drying the aqueous solution, wherein the water content after drying being in the range of 0-5 wt % to form a dried mixture;
3. heating the dried mixture to a temperature in the range from 60 to 180° C. to form a melt, and mixing the melt with fatty acid alkyl esters or triglycerides to form a reaction mixture;
4. optionally, intermediately storing and mixing the reaction mixture in a continuously operated stirred tank;
5. carrying out reaction in a tube reactor; and optionally
6. removing any coproducts.

2. The continuous process as claimed in claim 1, wherein the fatty acid alkyl esters or fatty acid triglycerides have a chain length of $C_4$ to $C_{50}$.

3. The continuous process as claimed in claim 1, wherein at least one N-n-alkylated polyhydroxyamine is a $C_1$ to $C_{12}$ N-alkylglucamine.

4. The continuous process as claimed in claim 1, wherein the concentration of the at least one N-n-alkylated polyhydroxyamine in the aqueous solution in the first process step is in the range from 30-90% by weight.

5. The continuous process as claimed in claim 1, wherein the catalyst is used in a concentration of 0.01-5 wt %.

6. The continuous process as claimed in claim 1, wherein the molar ratio of the at least one N-n-alkylated polyhydroxyamine:fatty acid alkyl ester is 1:0.85 to 1:1.2 or the molar ratio of the at least one N-n-alkylated polyhydroxyamine:fatty acid triglycerides is 0.25:1 to 0.45:1.

7. The continuous process as claimed in claim 1, wherein the mixing of raw material solution in the first step takes place at a temperature in the range of 40-120° C.

8. The continuous process as claimed in claim 1, wherein the carrying out reaction in a tube reactor takes place at a temperature in the range of 60-300° C. under a pressure in the range from 0 to 200 bar.

9. The continuous process as claimed in claim 1, wherein the temperature difference between a tube reactor wall and core flow in the tube reactor is <20° C.

10. The continuous process as claimed in claim 1, wherein phase transfer substances are added to the reaction mixture in one or more of the first three process steps.

11. The continuous process as claimed in claim 10, wherein phase transfer substances used comprise water, alcohols, glycols, N-alkylglucamides, polyalkylglycols, crown ethers and/or glycerol.

12. The continuous process as claimed in claim 1, wherein the polyhydroxy-fatty acid amides of the formula (1) have a (Gardner) color number in the range from 0 to 3.

13. The continuous process as claim 1, wherein the coproducts comprise cyclic byproducts and the fraction of cyclic byproducts in the resulting polyhydroxy-fatty acid amides of the formula (1) is <0.05 wt %.

14. The continuous process as claimed in claim 1, further comprising a blending step with solvents or solvent mixtures which may optionally comprise further additives.

* * * * *